(12) United States Patent
Berger (10) Patent No.: US 8,123,742 B2
(45) Date of Patent: Feb. 28, 2012

(54) CATHETER AND METHOD FOR ABLATION OF ATRIAL TISSUE

(75) Inventor: Ronald D. Berger, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1321 days.

(21) Appl. No.: 10/576,424

(22) PCT Filed: Oct. 20, 2004

(86) PCT No.: PCT/US2004/034864
§ 371 (c)(1),
(2), (4) Date: Mar. 13, 2007

(87) PCT Pub. No.: WO2005/041753
PCT Pub. Date: May 12, 2005

(65) Prior Publication Data
US 2007/0270789 A1    Nov. 22, 2007

Related U.S. Application Data

(60) Provisional application No. 60/512,657, filed on Oct. 20, 2003.

(51) Int. Cl.
*A61B 18/04* (2006.01)
(52) U.S. Cl. .............................. 606/27; 606/41
(58) Field of Classification Search ............... 606/27–41
See application file for complete search history.

(56) References Cited

U.S. PATENT DOCUMENTS

| | | | |
|---|---|---|---|
| 5,551,426 A | 9/1996 | Hummel et al. | |
| 5,749,825 A * | 5/1998 | Fischell et al. | 600/3 |
| 5,971,983 A * | 10/1999 | Lesh | 606/41 |
| 6,527,769 B2 * | 3/2003 | Langberg et al. | 606/41 |
| 6,633,780 B1 | 10/2003 | Berger | |
| 6,652,517 B1 * | 11/2003 | Hall et al. | 606/41 |
| 6,827,695 B2 | 12/2004 | Palazzolo et al. | |
| 6,865,413 B2 | 3/2005 | Halperin et al. | |
| 2002/0002329 A1 | 1/2002 | Avitall | |
| 2002/0087208 A1 | 7/2002 | Koblish et al. | |
| 2002/0111618 A1 | 8/2002 | Stewart et al. | |
| 2002/0165535 A1 | 11/2002 | Lesh et al. | |
| 2003/0050557 A1 | 3/2003 | Susil et al. | |
| 2003/0083613 A1 | 5/2003 | Schaer | |
| 2003/0130697 A1 | 7/2003 | Halperin et al. | |
| 2003/0199755 A1 | 10/2003 | Halperin et al. | |
| 2004/0082888 A1 | 4/2004 | Palazzolo et al. | |
| 2004/0147965 A1 | 7/2004 | Berger | |
| 2004/0210170 A1 | 10/2004 | Palazzolo et al. | |

\* cited by examiner

*Primary Examiner* — Linda Dvorak
*Assistant Examiner* — Amanda Scott
(74) *Attorney, Agent, or Firm* — Edwards Wildman Palmer LLP; Peter F. Corless; Melissa Hunter-Ensor (57) ABSTRACT

Featured is a catheter device for ablating tissue that includes an elongated body member having a distal portion and a deflection mechanism operably coupled to the distal portion so as to cause the distal portion to deflect with respect to a longitudinal axis of the elongated body member. Such a catheter device also includes a guide member and a guiding mechanism that is coupled to the elongated body member and is configured so as to guide the guide member. The guiding mechanism includes an exit portion from which the guide member exits during deployment. The exit portion is disposed with respect to the distal portion end so the distal portion deflects from and with respect to the guide member as well as rotating about the guide member. Also featured are systems and methods related thereto.

34 Claims, 8 Drawing Sheets

CATHETER AND METHOD FOR ABLATION OF ATRIAL TISSUE

This application claims the benefit of U.S. Provisional Application Ser. No. 60/512,657 filed Oct. 20, 2003, the teachings of which are incorporated herein by reference.

FIELD OF INVENTION

The present invention generally relates to surgical methods and devices for ablation of tissue; more particularly, to methods and devices embodying catheters for ablation of atrial tissue. The devices and methods are particularly suitable for the treatment of arrhythmias, and, in particular, catheter ablation for treatment of aroxysmal atrial fibrillation.

BACKGROUND OF THE INVENTION

Atrial fibrillation is the most common sustained arrhythmia and may increase the heart rate to, and in excess of, 100 to 175 beats per minute. It is associated with a high incidence of symptoms (e.g., atria quiver rather than contracting normally) and with multiple medical sequelae including strokes, blood pooling in the atria, and the formation of blood clots.

Recently, clinical investigators have found that in many cases, atrial fibrillation is initiated, and possibly maintained, by electrical triggers located in the pulmonary veins, Haissaguerre M, Jais P, Shah D C, Takahashi A, Hocini M, Quiniou G, Garrigue S, Le Mouroux A, Le Metayer P, Clementy J.; Spontaneous initiation of atrial fibrillation by ectopic beats originating in the pulmonary veins; N Engl J Med. 1998; 339(10):659-66. It also has been suggested that this can be cured or greatly suppressed by electrically isolating the pulmonary veins from the left atrium, Haissaguerre M, Jais P, Shah D C, Garrigue S, Takahashi A, Lavergne T, Hocini M, Peng J T, Roudaut R, Clementy J.; Electrophysiological end point for catheter ablation of atrial fibrillation initiated from multiple pulmonary venous foci; Circulation 2000; 101(12): 1409-17.

A variety of different atrial fibrillation treatment techniques are available, including drugs, surgery, implants, and catheter ablation. While drugs may be the treatment of choice for some patients, drugs typically only mask the symptoms and do not cure the underlying cause. Anti-arrhythmia drugs are disclosed, for example, in U.S. Pat. Nos. 4,558,155, 4,500,529, 4,988,698, 5,286,866 and 5,215,989. Also, the treatment of atrial arrhythmia by pharmaceuticals has been described in a number of medical articles and books including, for example, Martin, D., et al., Atrial Fibrillation, pgs. 35-41 (1994); Falk, R. H., et al., Atrial Fibrillation (1992); Singer, I., et al., Clinical Manual of Electrophysiology (1993); and Horowitz, L. N., Current Management of Arrhythmias (1991).

Implantable devices, on the other hand, usually correct an arrhythmia only after it occurs. See, for example, U.S. Pat. Nos. 5,282,836, 5,271,392 and 5,209,229 and Martin, D., et al., Atrial Fibrillation, pgs. 42-59 (1994) as to the use of an implanted atrial defibrillator or cardioversion. Implants, however, require a surgical procedure to be performed to install the implant, along with the risks associated with such procedures.

Surgical and catheter-based treatments, in contrast, can cure the problem by electrically isolating the ectopic foci responsible for the atrial fibrillation. An example of such a surgical procedure for the treatment of atrial arrhythmia is the "Maze" procedure that is discussed in Cox, J. L. et al., Electrophysiology, Pacing and Arrhythmia, "Operations for Atrial Fibrillation," Clin. Cardiol. Vol. 14, pgs. 827-834 (1991). See also Cox, J. L., et al., "The Surgical Treatment of Atrial Fibrillation," The Journal of Thoracic and Cardiovascular Surgery, Vol. 101, No. 4, pgs. 569-592 (April, 1991), and Cox, J. L., et al., "The Surgical Treatment of Atrial Fibrillation," The Journal of Thoracic and Cardiovascular Surgery, Vol. 101, No. 4, pgs. 406-426 (March, 1991). Other surgical procedures for atrial arrhythmia are discussed, for example, in Martin, D., et al., Atrial Fibrillation, pgs. 54-56 (1994).

In the catheter based treatments, atrial fibrillation is addressed or treated by ablating the abnormal tissue or electrically active tissue responsible for the atrial fibrillation (i.e., electrically isolating the accessory pathway responsible for the atrial fibrillation). The catheter-based treatment techniques rely on the application of various destructive energy sources to the target tissue, including direct current electrical energy, radio frequency electrical energy, laser energy, thermal (heat) energy (resistive element), cryo-thermal (cold) energy and the like. The ablation energy source, such as an ablating electrode, is normally disposed along a distal portion of the catheter.

A variety of catheter-based ablation strategies have been pursued to effect electrical isolation of the pulmonary veins. In such ablation strategies, electrophysiologists contemplate forming or placing ablative lesions at the pulmonary vein ostia, or even in the left atrium proper (see Pappone C, Rosanio S, Oreto G, Tocchi M, Gugliotta F, Vicedomini G, Salvati A, Dicandia C, Mazzone P, Santinelli V, Gulletta S, Chierchia S., Circumferential radiofrequency ablation of pulmonary vein ostia: A new anatomic approach for curing atrial fibrillation. Circulation, 2000; 102(21):2619-28).

Initially, electrophysiologists used standard radiofrequency (RF) ablation catheters to place a sector or ring of lesions inside the proximal segment of these veins. This technique was found to be problematic because success was limited due to the frequent incidence of arrhythmic triggers located at the pulmonary vein ostia (proximal to the ablative lesions), and the procedure carried an unacceptably high complication rate due to the subsequent development of pulmonary vein stenosis. Several catheters have been developed to apply circumferential lesions just inside the pulmonary veins using RF energy, ultrasound, or thermal energy. Catheters also have been developed to form circumferential lesions on the chamber wall about the pulmonary ostium and/or linear lesions on the chamber wall that extend between adjacent pulmonary veins.

Figure 1A:
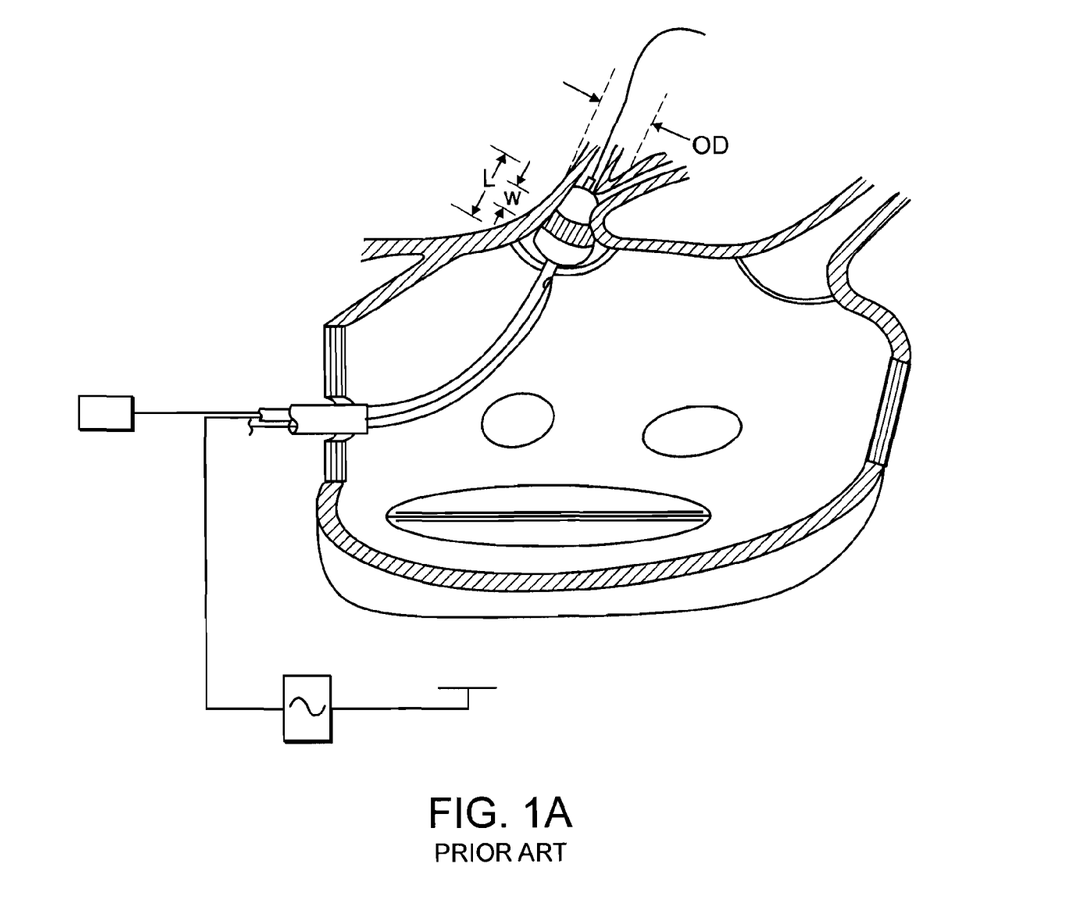
FIG. 1A is a perspective view of a prior art circumferential ablation assembly as described in U.S. Pat. No. 6,012,457, this figure more particularly corresponds to FIG. 5 of the '457 patent and thus reference shall be made to the '457 patent for further details for this figure.
Figure 1B:
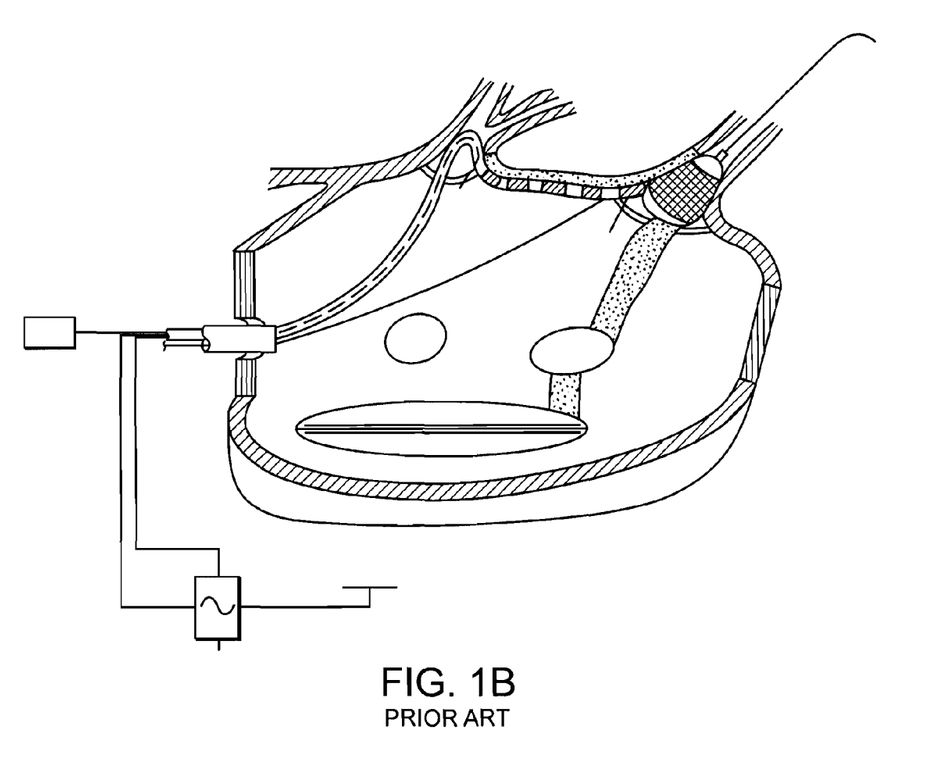

There is found in U.S. Pat. No. 6,012,457 and in U.S. Pat. No. 6,024,740 a device for forming a circumferential conduction block in a pulmonary vein (see FIG. 1A) and a device whereby a circumferential block is formed in a pulmonary vein and a linear lesion is formed between two adjacent pulmonary veins (see FIG. 1B). The devices employ an inflatable balloon to engage the pulmonary vein and to deliver energy in a radially symmetrical pattern to the vein. A guide wire is used to guide the balloon member into the pulmonary vein; however, the inflatable balloon and the ablative energy sources contained within it makes the use of the device complex. Also, while the system expedites pulmonary vein isolation, it is complex to manufacture and does not solve the fundamental difficulties associated with ablating inside the pulmonary veins, listed above.

Figure 1C:
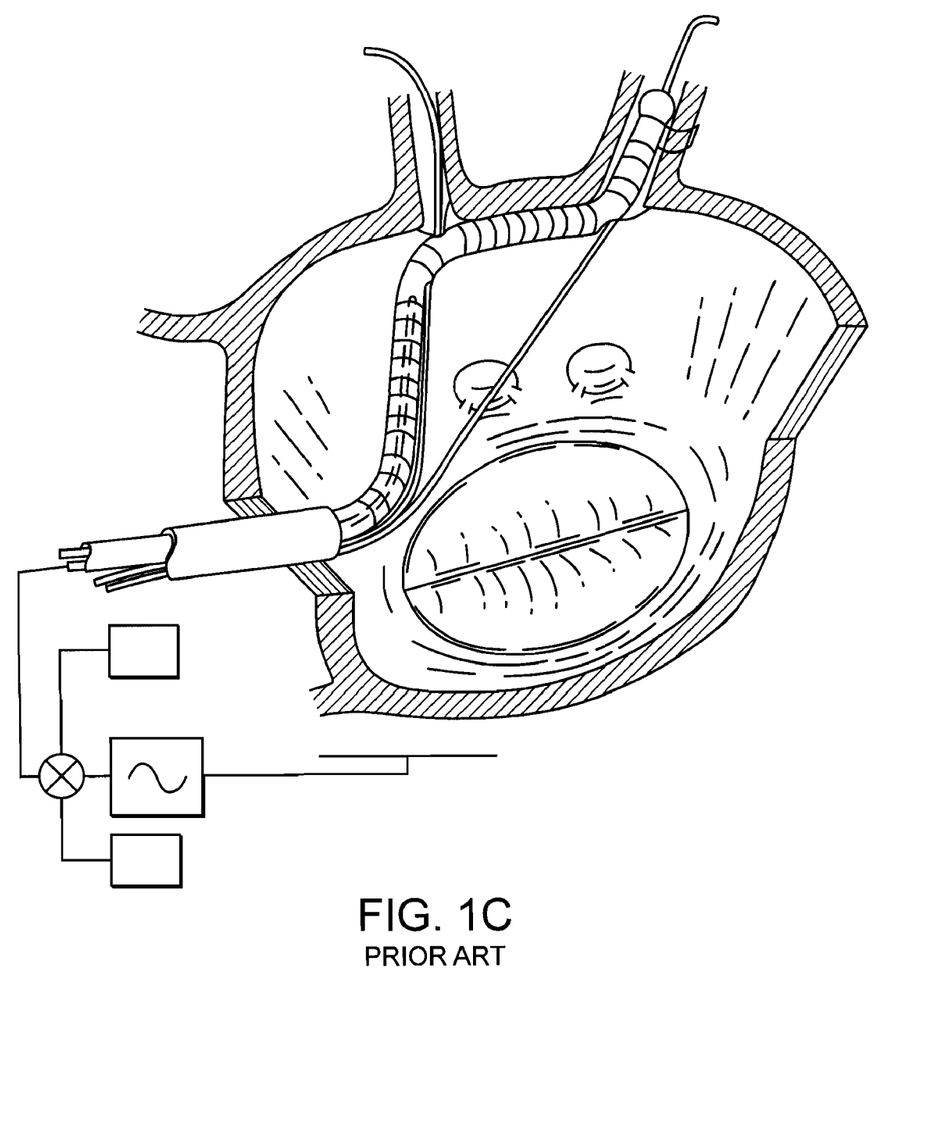
FIG. 1C is a perspective view of a prior art atrial lesioning catheter assembly as described in U.S. Pat. No. 5,971,983, this figure more particularly corresponds to FIG. 3 of the '983 patent and thus reference shall be made to the '983 patent for further details for this figure.

There is found in U.S. Pat. No. 5,971,983 a device for forming a circumferential block in a pulmonary vein and for forming a linear lesion formed between two adjacent pulmonary veins (see FIG. 1C). The described ablation device includes first and second ends that are bordered by first and second anchors and the anchors are adapted to secure the ablation element ends at predetermined first and second locations along the body space wall. In this way, the ablation device is adapted to ablate an elongate region of tissue between those locations. The anchors may be guidewire tracking members, each including a bore adapted to receive and track over a guidewire (one for each bore), and anchor within adjacent pulmonary vein ostia when the engaged guidewires are positioned within the respective veins. The device uses an inflatable balloon or similar strategies to engage the pulmonary vein and deliver energy in a radially symmetrical pattern. While the system expedites pulmonary vein isolation, it is complex to manufacture and does not solve the fundamental difficulties associated with ablating inside the pulmonary veins, listed above.

There is found in U.S. Pat. No. 5,938,660 devices that use two inflatable balloons to engage the pulmonary vein. For one of the described devices, RF energy is used to ablate the tissue between the balloons. For another of the described devices, the two balloons are inflated to form a seal that isolates the tissues there between and a chemical ablative material is introduced between the two balloons thereby ablating the tissues. The seals formed by the balloons are intended to prevent the chemical ablative material from escaping.

Figure 1D:
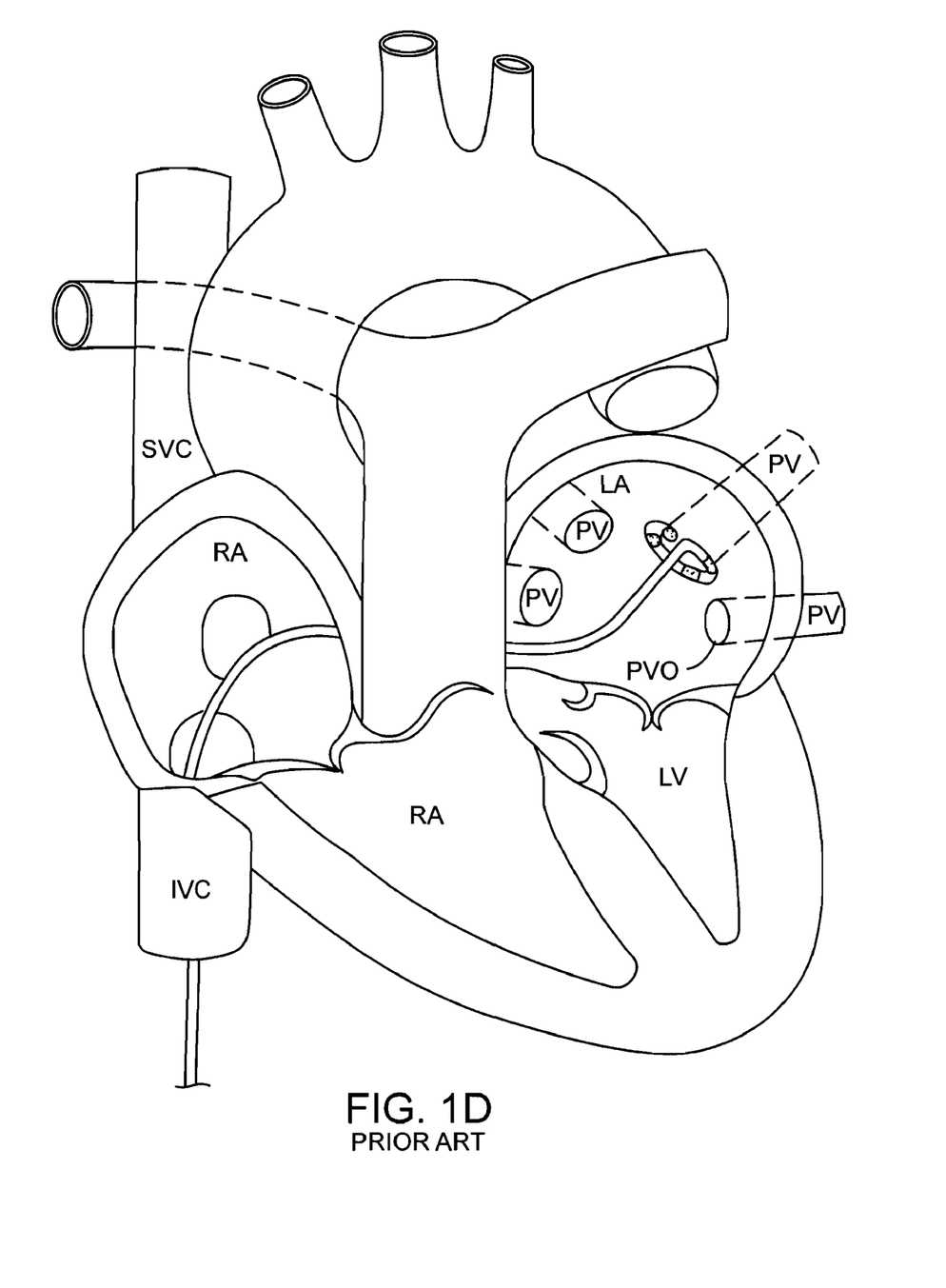
FIG. 1D is a perspective view of a prior art circumferential ablation assembly as described in U.S. Pat. No. 6,325,797, this figure more particularly corresponds to FIG. 2B of the '797 patent and thus reference shall be made to the '457 patent for further details for this figure.

There is found in U.S. Pat. No. 6,325,797 a catheter assembly including a distal portion that forms a substantially closed loop transverse to the longitudinal axis of the catheter body, where at least one electrode is provided along the loop. In use, the loop is axially directed into contact with the chamber wall about the vessel ostium (See FIG. 1D). When the at least one electrode is energized, the electrode ablates a continuous lesion pattern about the vessel ostium so as to electrically isolate the vessel from the chamber.

The goal in such cases is to electrically isolate the pulmonary veins, but to do so with a wider ring of lesions and without placing lesions inside the pulmonary veins themselves. It is, however, technically more challenging to place a set of contiguous lesions in a large ring outside the pulmonary vein than to create a ring of lesions inside the vein. Also for other types of ablation catheters, the ablation catheter tends to fall away from the wall of the left atrium as it is moved from point to point, making contiguity of the lesions difficult to achieve. Procedure times are often long and fluoroscopic radiation exposure can be substantial. Electroanatomical mapping techniques have been used to mitigate these problems, but manipulation of the catheter to the many sites required for creation of large isolating rings of ablative lesions remains challenging, particularly due to the irregular three-dimensional shape and trabeculated endocardial surface of the left atrium.

There is found in U.S. Pat. No. 6,241,728 a left atrium ablation catheter including a deflectable eletrophysiology catheter having ablation electrodes along the tip thereof. It is further described that the electrode tip is sized and configured to create the desired lesion at the target site without movement of the electrode tip along the target site.

A recently introduced ultrasound ablation balloon system is designed to apply a ring of lesions at the pulmonary vein ostium instead of inside the vein (see Meininger G R. Calkins H. Lickfett L. Lopath P. Fjield T. Pacheco R. Harhen P. Rodriguez E R. Berger R. Halperin H. Solomon S B. Initial experience with a novel focused ultrasound ablation system for ring ablation outside the pulmonary vein. J. Interventional Cardiac Electrophysiol. 8:141-148, 2003). This system is complex and will place lesions distal to arrhythmic triggers located peri-ostially.

It thus would be desirable to provide a new device(s) for ablating tissue so as to form lesions as well as systems and methods related thereto. It would be particularly desirable to provide such a device, system, and method which embodies a guide member for localizing the ablation mechanism with respect to the tissue surface and which guide member provides a mechanism by which the ablation mechanism can be easily and continuously repositioned with respect to the tissues (e.g. rotated about the guide member), thereby to form a circumference of such lesions. It also would be desirable to provide such devices that can form such a circumference of lesions more easily and with less risk as compared to prior art devices as well as making continguity of the lesions easier to achieve as compared to prior art devices. Such collection devices preferably would be simple in construction as compared to prior art devices.

SUMMARY OF THE INVENTION

The present invention features a catheter device that is usable for ablating tissue as well as systems and methods related thereto. In its broadest aspects the catheter device of the present invention includes an elongated body member having a distal portion and a deflection mechanism operably coupled to the distal portion so as to cause the distal portion to deflect with respect to a longitudinal axis of the elongated body member. As is known to those skilled in the art, the elongated body portion is configured and arranged (e.g., sized) so that the catheter can be introduced into the circulatory system and passed through portions of the circulatory system so the operable end of the catheter (distal portion) can be localized to the tissue to be treated and/or analyzed. For example, the operable end of the catheter can be located in the left atrium of a mammalian heart so that appropriate measurements can be made to determine or identify a pulmonary vein(s) that should be electrically isolated and/or to ablate tissue so as to electrically isolate portions of the nervous system of the heart from tissues of the pulmonary vein.

Such a catheter device according to the present invention further includes a guide member and a guiding mechanism that is coupled to the elongated body member and is configured so as to guide the guide member during its deployment The guiding mechanism includes an exit portion from which the guide member exits when the guide member is being deployed from the guiding mechanism. The exit portion is disposed with respect to the distal portion so the distal portion deflects from and with respect to the guide member, when the guide member is in deployed condition.

In use, the guide member is deployed from the guiding mechanism end portion so that portions of the guide member, including the distal end, are introduced/deployed through an opening in a chamber, vessel or vein (e.g., pulmonary vein) of the mammalian body, thereby localizing the guide member and the elongated body member with respect to the opening. In more particular embodiments, the guide member also secures the elongated body member in a relatively fixed non-contact relation with respect to the body opening so that, as herein described, the deflection mechanism can deflect the distal portion of the elongated body member with respect to the guide member and thus place the operable end of the distal portion in contact with the tissues to be ablated. Also, the guide member secures the elongated body member in a relatively fixed relation with respect to the body opening so as to allow the distal portion to be moved about the guide member (e.g. rotated about an axis formed by the guide member).

In a particular embodiment, the guide member is a guide wire. The guide member, however, shall not be construed as being limited to just the wire form or configuration. It is contemplated and thus within the scope of the present invention for any other structure known to those skilled in the art, that is appropriate for the intended use, such as for example a flat elongated member or hollow elongated tubular member to be used with the catheter device of the present invention. Also, while a generally cylindrical or circular shape is illustrated herein, the guide member can have any geometric shape, such as for example hexagonal, that otherwise is appropriate for the given application.

The guiding mechanism comprises any of a number of structures known to those skilled in the art adaptable for use with the present invention. Such a mechanism preferably is characterized as being capable of moveably retaining or moveably securing the guide member so the user can deploy the guide member from the guiding mechanism/catheter. In an embodiment/aspect of the present invention, the guiding mechanism comprises a channel, lumen or passage provided within the elongated body member of the catheter proper or comprises a device, element or structure that is secured to the exterior surface of the elongated body that is configured and arranged so as to provide such a channel, lumen or passage.

In this aspect/embodiment, the channel, lumen or passage is configured and arranged so that the guide member is slidably or moveable retained within the channel, lumen or passage. In other embodiments/aspects, the guiding mechanism further includes a through aperture formed in a side of the elongated body member in communication with the channel or a through aperture in a side or end of the element or structure that is secured to the elongated body member. In this way, the distal end of the guide member passes through the through aperture when the guide member is being deployed from the channel, lumen or passage.

In another embodiment, the guiding mechanism is a structural feature or artifact that is secured, affixed or formed in an exterior surface of the elongated body member. Also, the structural feature or artifact and the guide member are each configured and arranged so as to cooperate and form a mechanical connection that movably secures the guide member to the structural feature or artifact In an illustrative, exemplary embodiment, the guide mechanism is in the form of a rail that extends along the length of the elongated body member. In addition, the guide member is configured and arranged so as to movably engage a portion or structural element of the rail so that the guide member is essentially prevented from moving in directions other than along the length of the rail.

In further aspects/embodiments, the end point of the guiding mechanism (e.g., the through aperture in the side of the elongated member or the end of the rail) is positioned with respect to the end of the distal portion of the elongated member so that the end point is in a predetermined relation with respect to a deflection point of the distal portion. As is known to those skilled in the art, a catheter having a deflection mechanism is configured so that the distal portion of the elongated body member will deflect or move (e.g., curve) with respect to a longitudinal axis of the elongated body member and about a specific point from the end of the distal portion. For example, groups of wires are attached or secured to the distal portion and are arranged so that when they are operated in specific ways, the distal portion of the catheter is moved with respect to the long axis of the body member. As is also known to those skilled in the art, such deflection mechanisms can be arranged and operated so that the end of the distal portion can be deflected or curved back upon itself so the end is pointing in a direction that is opposite to the general direction of other portions of the elongated body member (e.g., forming a hook like arrangement).

In a more particular specific aspect/embodiment of the present invention, the end point of the guiding mechanism is located so as to be within a predetermine range of values on either side of the point of deflection. In more specific embodiments, the end point is located so as to be one of in proximity to the deflection point, proximal to the deflection point, or at about the deflection point. In further embodiments, the end point of the guiding mechanism is arranged with respect to the end of the distal portion of the elongated member so as to allow the deflected end to be rotated about the guide member, preferably so that the end of the distal portion traverses a circumference of a circle. Because, many of the openings are circular, near circular or oval in nature, the end of the distal portion of the elongated body member about the guide member should be generally maintained in contact with the tissue as the end is being rotated about the guide member. Also, such contact is achieved in the present invention without a significant increase in the forces being applied to the tissues being contacted as compared to the forces being applied when using prior art devices.

In further embodiments, the catheter device includes a mechanism for ablating tissue that is disposed at or about the end or end portion of the distal portion of the elongated body member, particularly as the end portion is being rotated about the guide member. The ablation mechanism is configured and arranged so as to embody any one of a number of techniques known to those skilled in the art for ablating tissue and appropriate for the intended use. In particular embodiments, the ablation mechanism is configured and arranged so ablation is caused by one of RF energy, thermal energy, cryothermal energy, ultrasound or laser energy/light techniques. Such techniques for ablating tissue are well known to those skilled in the art and thus, one skilled in the art can readily adapt the catheter device of the present invention so as to be capable of ablating tissue using any one or more of these techniques.

Also featured is a system embodying such a catheter device and methods for treating including ablating tissue relating to such a catheter device and/or system.

Other aspects and embodiments of the invention are discussed below.

DEFINITIONS

The instant invention is most clearly understood with reference to the following definitions:

The term "ablation" or derivatives thereof shall be understood to mean the substantial altering of the mechanical, electrical, chemical, or other structural nature of the tissue. In the context of intracardiac ablation applications as shown and described with reference to the embodiments below, ablation is intended to mean sufficient altering of the tissue properties to substantially block conduction of electrical signals from or through the ablated cardiac tissue.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIG. 1B is a perspective view of another prior art circumferential ablation assembly as described in U.S. Pat. No.

6,012,457 for forming at least one linear lesion, this figure more particularly corresponds to FIG. 9D of the '457 patent and thus reference shall be made to the '457 patent for further details for this figure;

DESCRIPTION OF THE PREFERRED EMBODIMENT

Figure 2A:
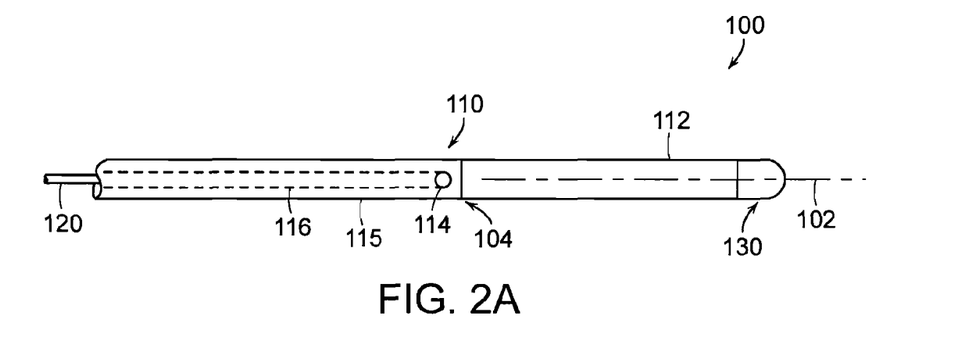
FIG. 2A is a schematic view of a catheter of the present invention when the guide member has not been deployed.
Figure 2B:
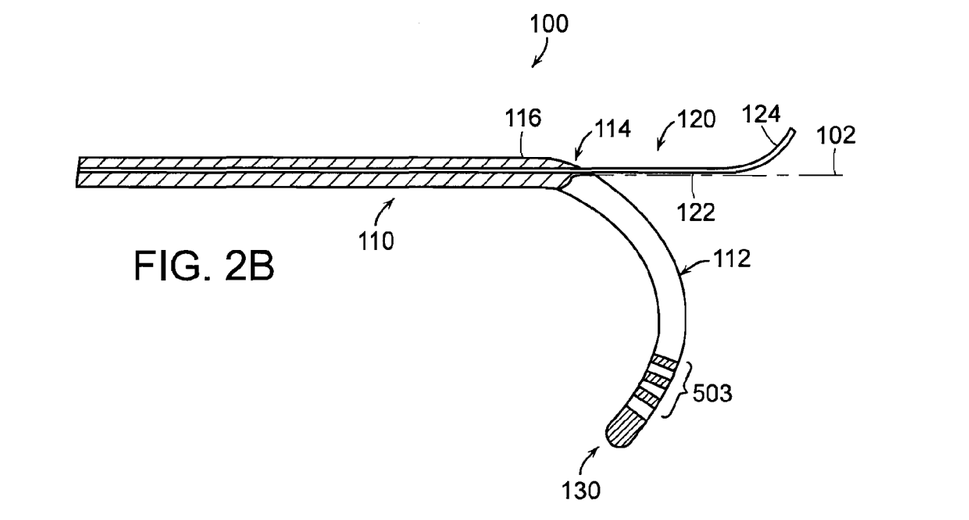
FIG. 2B is a partial cross-sectional side view of the catheter of FIG. 2A but with the guide member deployed and the distal end being deflected.

Referring now to the various figures of the drawing wherein like reference characters refer to like parts, there is shown in FIGS. 2A,B various views of a catheter device 100 according to an aspect of the present invention that is configured and arranged for ablation of tissue. Such a catheter device includes an elongated body member 110 having a distal portion 112 and a deflection mechanism that is operably coupled to the distal portion so as to cause the distal portion to deflect with respect to a longitudinal axis 102 of the elongated body member.

As is known to those skilled in the art, the elongated body portion 110 is configured and arranged (e.g., sized) so that it can be introduced into the circulatory system and passed through portions of the circulatory system so the end of the distal portion 112 of the catheter device 100 can be localized to the tissue to be treated and/or analyzed. For example, the operable end of the distal portion 112 can be located in the left atrium of a mammalian heart so that appropriate measurements can be made to determine or identify a pulmonary vein(s) that should be electrically isolated and/or to ablate tissue using the catheter device so as to electrically isolate the nervous system of the heart from tissues of the pulmonary vein.

As is also known in the art, a catheter device such as that of the present invention can be configured and arranged with any one of a number of devices or mechanisms, herein referred to as a deflection mechanism, that can be actuated or operated so as to cause a distal portion 112 of the elongated body member 110 to deflect or be moved with respect to the longitudinal axis 102 of the elongated body member. For example, groups of wires are attached or secured to the distal portion and are arranged so that when they are operated in specific ways, the distal portion of the catheter is moved with respect to the long axis of the body member. In a particularly illustrative example and as illustrated in FIG. 2B, the deflection mechanism causes the distal portion 112 to be deflected with respect to a deflection point 104.

Depending upon the characteristics and capabilities of the deflection mechanism, the deflection mechanism can be operated so as to cause the distal portion 112 to be deflected so as take any of a number of forms and configurations. In a particularly illustrative example as shown in FIG. 2B, the deflection mechanism reconfigures the distal portion so as to be curved or arcuate. In a specific illustrative embodiment, the deflection mechanism cause the distal portion 112 to be reconfigured or deflected so that the distal portion curves back upon the elongated body 110 so that the end of the distal portion is being directed in part in a direction that is generally opposite to the direction the rest of the elongated body 110 as shown in FIG. 2B.

As is also known in the art, a handle or actuation mechanism/device is operably coupled to the deflection mechanism and that operates or actuates the deflection mechanism so as to cause a distal portion 112 of the elongated body member 110 to deflect or be moved with respect to the longitudinal axis 102 of the elongated body member. For example the handle or actuation mechanism/device is operably coupled to groups of wires that are attached or secured to the distal portion. The handle or actuation mechanism/device is further arranged so that they act on the wires in specific ways so as to cause the distal portion of the catheter to be moved with respect to the long axis of the body member. The handle or actuation mechanism is remote from the distal end 112 of the elongated body member 110 and also is located external to the mammalian body in which the elongated body member has been inserted into.

Such a handle or actuation mechanism/device typically includes a port that would be operable coupled to the lumen, passage or channel 116 so the guide member 120 would be inserted into and operated through such a port. Alternatively, the handle or actuation mechanism/device would be adapted so as to include such a port that would be operable coupled to the lumen, passage or channel 116. In yet further embodiments, the handle or actuation mechanism/device is configured and arranged so as to include a device that is operably coupled to the guide member 120 so actuation of the device causes the guide member to be deployed from and retracted into the guiding mechanism.

Reference shall be made to U.S. Pat. Nos. 4,960,134; 4,911,148; 5,254,088; 5,318,525; 5,441,483; and 5,456,664, as to further details and discussions of various types and forms of exemplary deflection mechanisms and/or catheters having such deflection mechanisms, which deflection mechanisms are adaptable by one skilled in the art for use with the catheter device 100 of the present invention. Reference also shall be made to U.S. Pat. Nos. 4,960,134; 4,911,148; 5,254, 088; 5,318,525; 5,441,483; and 5,456,664, as to further details and discussions of various types and forms of exemplary the handles or actuation mechanisms/devices that are operably coupled to the deflection mechanisms. In this regard the teachings of the above identified patents/publication are incorporated herein by reference.

The catheter device 100 of the present invention also includes a guiding mechanism or device that is configured and arranged so as to retain the guide member 120 as the catheter device is being manipulated so the operable end thereof is proximal the target locus or target site. The guiding mechanism or device also is configured and arranged so the guiding mechanism moveably retains the guide member 120 so a distal end 124 of the guide member can be deployed therefrom and extended into a vessel, opening or vein of a mammalian body and so other portions of the guide member remain or are essentially secured to the elongated body member 110.

In an aspect/embodiment of the present invention, the guiding mechanism comprises a lumen, passage or channel 116 that is disposed within the elongated body member 110, which passage, lumen or channel is arranged so as to extend along the longitudinal axis of the elongated body member. Although the guiding mechanism is illustrated as being generally parallel to the long axis, it shall be understood that the term along the long axis also includes the lumen, passage or channel 116 being arranged in any of a number of fashions with respect to the long axis (e.g., helical) that also extends along the long axis. The lumen, passage or channel 116 is formed in the structure comprising the elongated body member 110 or comprises a device, structure or longitudinally extending member (e.g., tubular member) that is disposed within the elongated body member and is arranged so as to extend along the longitudinal axis of the elongated body member. Such a device, structure or longitudinally extending member is further configured and arranged so as to included a lumen, passage or channel 116 therein and running along the long axis of such device, structure or longitudinally extending member. The lumen, passage or channel 116 is sized and configured (e.g., formed) so the guide member 120 is moveable received within the channel; more particularly the guide member 120 is slidably disposed within the channel 116. In an illustrative, exemplary embodiment, the lumen, passage or channel 116 is configured so as to have a generally cylindrical or arcuate cross-section.

The guiding mechanism further includes an aperture 114 (e.g. a through aperture) or exit, in a wall of the elongated body member 110 that is in arranged so as to be in communication with or coupled to the lumen, passage or channel 116. The aperture 114 is located so as to be a predetermined distance back from the end of the distal portion 112 and so as to lie in a range of values with respect to the deflection point 104. In more particular embodiments, the aperture 114 is located on either side of side of the deflection point 104. In more specific embodiments, the aperture 114 is located so as to be any one of in proximity to the deflection point 104, proximal to the deflection point, at about the deflection point or at the deflection point.

In further embodiments and as more clearly illustrated in FIG. 2B, the aperture 114 is located on the side of the elongated member opposite to where the distal portion 112 deflects. As such, it can be seen that the distal portion 112 also deflects with respect to the guide member 120 when it is deployed and extending outwardly from the aperture.

As herein described, in further embodiments the guide member 120 also is preferably secured within the mammalian body so that the distal portion 112 of the guide member 120, when it is deflected, also can be moved about and with respect to the guide member (e.g., rotated). Accordingly, in further embodiments, the aperture 114 and the lumen, passage or channel 116 also are configured and arranged so as to allow the distal portion 112 of the elongated body member 110 to be moved about and with respect to the guide member, more specifically rotated about the guide member. In this way, the distal portion 112 can form lesions that have continuity about a circumference.

Figure 2C:
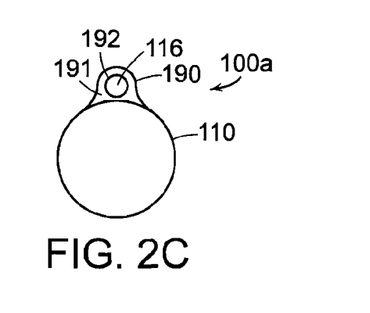
FIG. 2C is an end view of an alternate embodiment of a catheter device of FIG. 2A.

In an alternative embodiment and with reference to FIG. 2C, the guide mechanism comprises a device, structure or longitudinally extending member 190 (e.g., tubular member) that is affixed or secured to the exterior surface of the elongated body member 110 and is arranged so as to extend along the longitudinal axis 102 of the elongated body member. Alternatively, the elongated body member 110 is formed so that the device, structure or longitudinally extending member 190 (e.g., tubular member) is formed integral with the elongated body member 110. Such a device, structure or longitudinally extending member 190 also is configured and arranged so as to included a lumen, passage or channel 116 therein that runs along the long axis of such device, structure or longitudinally extending member. The guiding mechanism and the elongated body member 110 comprises any of a number of materials known in the art that are appropriate for the intended use, and more particularly comprise materials that are bio-compatible.

In this embodiment an end 191 of the device, structure or longitudinally extending member 190 is configured and arranged with an aperture 192 or exit that communicates with the channel 116. In this way, the guide member 120 can be deployed through the aperture 192.

Figure 3A:
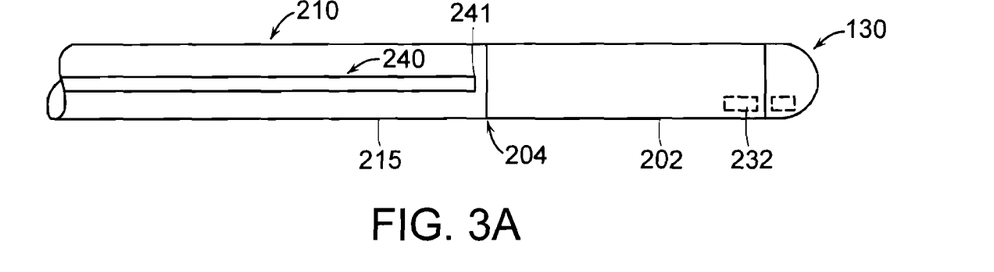
FIG. 3A is a schematic view of a catheter according to another aspect of the present invention when the guide member has not been deployed.

In addition, the end 191 of the device, structure or longitudinally extending member 190 is located so as to be a predetermined distance back from the end of the distal portion 112 so as to lie in a range of values with respect to the deflection point 104, such as that illustrated for the guiding mechanism 240 of FIG. 3A. In more particular embodiments, the elongated member end 191 is located on either side of side of the deflection point 104. In more specific embodiments, the elongated member end 191 is located so as to be any one of in proximity to the deflection point 104, proximal to the deflection point, at about the deflection point or at the deflection point.

Figure 3B:
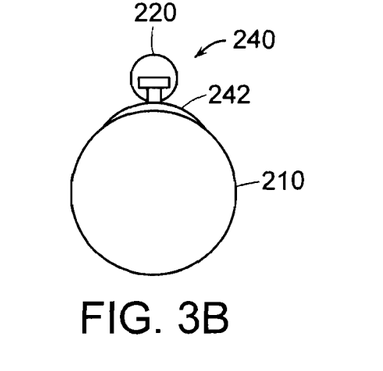
FIG. 3B is an end schematic view of the catheter of FIG. 3A to illustrate another embodiment of a guiding mechanism according to the present invention.

In further embodiments and as more clearly illustrated in FIGS. 2B/3B, the device, structure or longitudinally extending member 190 is located on the side of the elongated body member 110 that is opposite to where the distal portion 112 deflects. As such, it can be seen that the distal portion 112 also deflects with respect to the guide member 120 when it is deployed and extending outwardly from the aperture.

As herein described, in further embodiments the guide member 120 also is preferably secured within the mammalian body so that the distal portion 112 of the elongated body member 110, when it is deflected, also can be moved about and with respect to the guide member (e.g., rotated). Accordingly, in further embodiments, the aperture 192 and the lumen, passage or channel 116 in the device, structure or longitudinally extending member 190 also are configured and arranged so as to allow the distal portion 112 of the elongated body member 110 to be moved about and with respect to the guide member, more specifically rotated about the guide member.

The guide member 120 comprises any of a number of devices, members, elements or structures known to those skilled in the art, that is appropriate for the intended use, such as for example a flat elongated member, a hollow elongated tubular member or an elongated cylindrical member. While a generally cylindrical or circular shape is illustrated herein, the guide member 120 can have any geometric shape, such as for example hexagonal, that otherwise is appropriate for the given application. In further embodiments, the guide member 120 is configured and arranged so different portions of the guide member have different constructions and/or constitutions or make-up. For example, the distal portion 124 of the guide member 120 can be configured and arranged so for purposes of engaging tissues and other portions 122 of the guide member are configured and arranged so the elongated body member distal portion 112 can be moved about the guide member. In more illustrative exemplary embodiments, the guide member 120 comprises a guide wire. In preferred embodiments, such as guide wire is configured so as to have a stiff body and soft distal segment.

Suitable designs for the guide member 120 of the present invention may be selected from previously known designs of guide wires, while generally any suitable choice should be constituted so as to include a shaped, radiopaque distal end portion with a relatively stiff, torquable proximal portion adapted to steer the shaped tip under X-ray visualization. Guidewires or guide members 120 having an outer diameter ranging from 0.010" to 0.035" may be suitable. In cases where the guidewire or guide member is used to bridge the atrium from the guiding catheter at the fossa ovalis, and where no other sub-selective guiding catheters are used, guidewires having an outer diameter ranging from 0.018" to 0.035" may be required. Guidewires or guide members within this size range may be required to provide sufficient stiffness and maneuverability in order to allow for guidewire control and to prevent undesirable guidewire prolapsing within the relatively open atrial cavity.

Figure 3C:
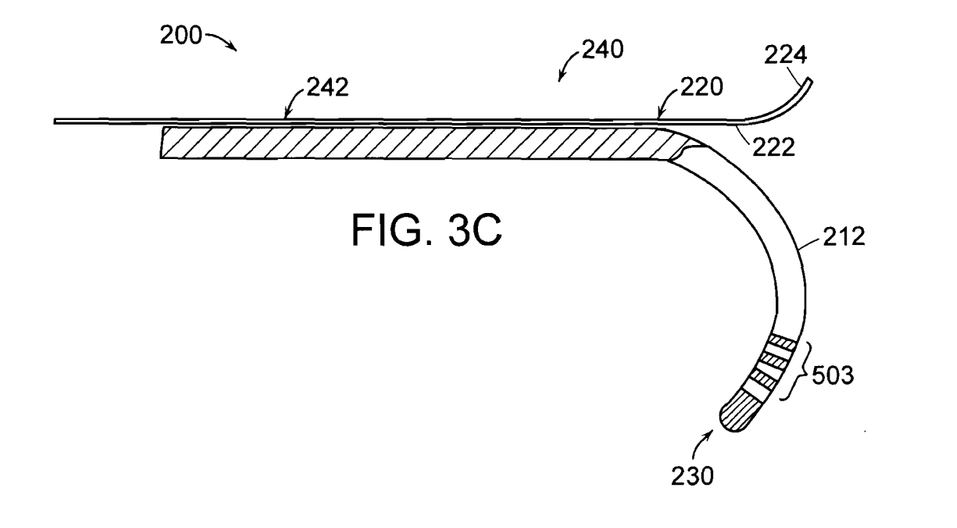
FIG. 3C is a schematic side view of the catheter of FIG. 3A but with the guide member deployed and the distal end being deflected.

According to another aspect/embodiment of the present invention, and with reference to FIGS. 3A-C, a catheter device 200 is configured and arranged so the guiding mechanism 240 includes a device, artifact, or structure 242 that is secured or affixed to an exterior surface of the elongated body member 210 and is arranged so as to extend along the longitudinal axis 102 of the elongated body member. Alternatively, the elongated body member 110 is formed so that the device, artifact or structure 242 is formed so as to be integral with the elongated body member 210.

In further embodiments, the device, artifact or structure 242 and the guide member 220 are each configured and arranged so as to cooperate and form a mechanical connection that movably secures the guide member 220 to the structure 242, thereby forming the guiding mechanism. In an illustrative, exemplary embodiment, the guide member 220 is in the form of a rail that extends along the length of the elongated body member 210 and the guide member 220 is configured and arranged with a axially extending slotted aperture that is configured so as to movably engage a portion or structural element of the rail so that the guide member is essentially prevented from moving in directions other than along the length of the rail.

In further aspects/embodiments, the end point 241 of the guiding mechanism 240 (e.g., the end of the rail) is positioned with respect to the end of the distal portion 212 of the elongated member 210 so that the end point 241 is in a predetermined relation with respect to a deflection point 104 of the distal portion. As is known to those skilled in the art, a catheter having a deflection mechanism is configured so that the distal portion 112, 212 of the elongated body member 110, 210 will deflect or move (e.g., curve) with respect to a longitudinal axis 102 of the elongated body member and about a specific point 104, 204 from the end of the distal portion. For example, groups of wires are attached or secured to the distal portion 112, 212 and are arranged so that when they are operated in specific ways, the distal portion of the catheter device 100, 200 is moved with respect to the long axis of the body member. As is also known to those skilled in the art, such deflection mechanisms can be arranged and operated so that the end of the distal portion 112, 212 can be deflected or curved back upon itself so the end thereof is pointing in a direction that is opposite to the general direction of other portions 115, 215 of the elongated body member 110, 210 (e.g., forming a hook like arrangement).

In more particular specific aspects/embodiments, the end point 201 of the guiding mechanism 240 is located so as to be within a predetermine range of values on either side of the point of deflection 204. In more specific embodiments, the end point 201 is located so as to be one of in proximity to the deflection point 204, proximal to the deflection point 204, at about the deflection point 204 or at the deflection point 204. In further embodiments, the end point 241 of the guiding mechanism 240 is arranged with respect to the end of the distal portion 212 of the elongated body member so as to allow the deflected end to be moved about and with respect to the guide member 220.

In more specific embodiments, the end of the distal portion 212 is rotated about and with respect to the guide member 220 preferably so that the end of the distal portion traverses a circumference of a circle. Because many of the openings are circular, near circular or oval in nature, the end of the distal portion 212 of the elongated body member 210, as it is being rotated about the guide member 220, should be generally maintained in contact with the tissue. Also, such contact is achieved in the present invention without a significant increase in the forces being applied to the tissues being contacted as compared to the forces being applied when using prior art devices.

In further embodiments, the catheter devices 100, 200 of the present invention include an ablation device or ablation mechanism 130, 230 that is disposed in the distal portion 112, 212. Although the ablation mechanism 130, 230 is illustrated as being disposed at or about the end of the distal portion 112, 212, this shall not be construed as limiting the ablation mechanism only to this configuration. It is well within the skill of those knowledgeable in the arts to appropriately locate the ablation mechanism 130, 230 within the distal portion 112, 212 based on the particular form of the ablation mechanism as herein described as well as the particulars of how the distal portion is deflected with respect to the guide member 120, 220 the deflection point 104,204.

An ablation mechanism 130, 230 in its broadest meaning is herein intended to mean an element, device or mechanism that is adapted to substantially ablate tissue in a body space wall upon activation by an actuator. Such an ablation mechanism 130, 230 includes, but is not limited to a discrete element, such as an electrode or an optical fiber, or a plurality of discrete elements, such as a plurality of spaced electrodes or optical fibers, which are positioned so as to collectively ablate an elongated region of tissue. As indicated herein, the catheter devices 100, 200 of the present invention are adaptable to ablate such tissue in a variety of ways. For example, one suitable ablation mechanism 130, 230 is adapted to emit energy sufficient to ablate tissue when coupled to and energized by an energy source. Suitable examples of energy emitting ablation mechanisms within this meaning include without limitation: an electrode element adapted to couple to a direct current (DC) or alternating current (AC) source, such as a radiofrequency (RF) current source; an antenna element that is energized by a microwave energy source; a heating element, such as a metallic element that is energized by heat such as by convection or current flow, or a fiber optic element which is heated by light; a light emitting element, such as a fiber optic element that transmits light sufficient to ablate tissue when coupled to a light source; or an ultrasonic element such as an ultrasound crystal element that is adapted to emit ultrasonic sound waves sufficient to ablate tissue when coupled to a suitable excitation source.

More detailed descriptions of radiofrequency (RF) ablation electrode designs that may be adaptable in whole or in part as the ablating mechanism 130, 230 according to the present invention are disclosed in U.S. Pat. No. 5,209,229 to Gilli; U.S. Pat. No. 5,487,385 to Avitall; and WO 96/10961 to Fleischman et al. More detailed descriptions of other energy emitting ablation elements that may be adaptable according to the present invention are disclosed in U.S. Pat. No. 4,641,649 to Walinsky et al. (microwave ablation); and U.S. Pat. No. 5,156,157 to Valenta, Jr. et al. (laser ablation). The disclosures of these patents are herein incorporated in their entirety by reference.

In addition, other ablation mechanisms for altering the nature of tissue may be suitable as an ablation mechanism 130, 230 of the present invention. For example, a cryoblation probe element adapted to sufficiently cool tissue to substantially alter the structure thereof may be adaptable for use with the catheter devices 100, 200 of the present invention. More detailed examples of cryoblation such as that just described are disclosed in U.S. Pat. No. 5,147,355 to Friedman et al. and WO 95/19738 to Milder, respectively. The disclosures of these patents are incorporated in their entirety by reference.

In more particular embodiments, the catheter devices 100, 200 of the present invention further include temperature-monitoring elements such as thermsistors or thermocouples. The inclusion of the thermistors or thermocouples provide a mechanism to measure the temperature in the region of the ablation mechanism 130, 230 for purposes of feedback control during the ablation procedure. In a further embodiment, each thermistors or thermocouple is positioned in the vicinity of one of the electrodes of an ablation mechanism 130, 230 or ablation element for example and is also coupled to a temperature monitoring leads. More detail regarding the particular size, material, dimensions, and methods of constructing the electrode and temperature monitoring elements onto a catheter may be found by reference to U.S. Pat. No. 5,582,609 to Swanson et al. the teachings of which are herein incorporated by reference.

Such temperature monitoring elements may be coupled directly to the electrodes, or may be otherwise positioned along the length of the ablation mechanism 130, 230 or ablation element as would be apparent to one of ordinary skill. The electrode and temperature monitoring designs herein described merely represent specific embodiments for use with the present invention. As such, it is contemplated that the catheter devices 100, 200 of the present invention can use any of a number of other temperature monitoring devices, systems and apparatuses as well as other temperature monitoring techniques that are appropriate for the given ablation technique embodied in the catheter device 100, 200 (e.g., a temperature monitoring technique and devices appropriate for cryoblation).

Figure 5:
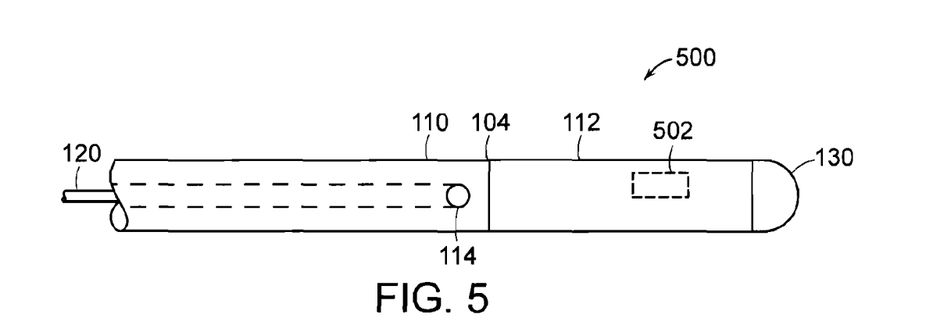
FIG. 5 is a schematic view of a catheter of an embodiment of the present invention, when the distal portion is configured to include a sensing element.

Referring now also to FIG. 5, there is shown an embodiment of a catheter device 500 according to the present invention. Such a catheter device 500 is configured and arranged so as to include any one of a number of devices or sensing elements or position sensor 502 known to those skilled in the art that is configured and arranged to allow for electroanatomical tracking. In further embodiments and as illustrated in FIGS. 2B, 3B; such a sensor 502 can comprise two electrodes 503 to establish a bipolar circuit, where the proximal electrode is used for mapping electrical activity.

Figure 6:
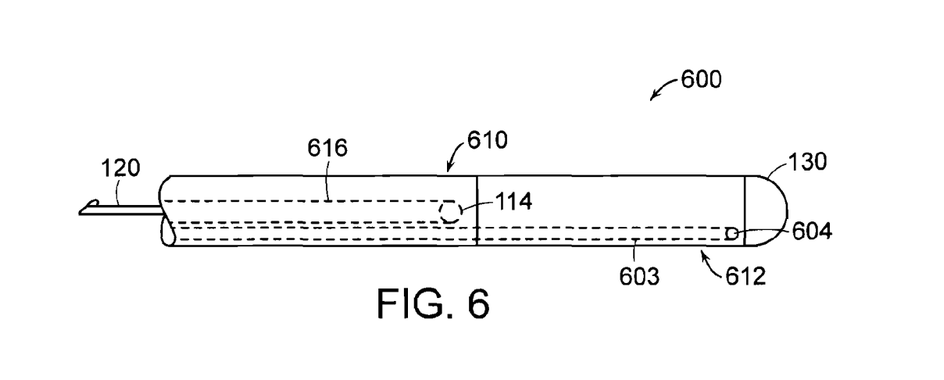
FIG. 6 is a schematic view of a catheter according to another embodiment of the present invention.

Referring now to FIG. 6, there is shown an embodiment of a catheter device 600 according to the present invention. For such a catheter device 600, the elongated body member 610 is configured and arranged so as to include another lumen, passage or channel 603, that extends along the length of the elongated body member and which communicates with a through aperture 604 in the distal portion 612 of the elongated body member. This additional channel also is operably coupled to a fluid source (not shown) so that this fluid can be delivered to enable cooling during delivery of thermal or RF energy. The through aperture 604 also is appropriately located in the distal portion 612 so that the fluid being delivered can have the intended or desired cooling effect.

In an alternative embodiment, said another channel 603 in the elongated body member 610 is arranged so as to form a closed loop, where the looped portion of the channel is disposed or located in the distal portion 612 of the elongated body member. In this alternative embodiment, one end of the channel upstream of the channel looped portion, would be connected to a fluid source (not shown) that supplies the cooling fluid, which would be passed through the looped portion. After passing through the looped portion, the fluid exits through the other end of the channel. The fluid exiting the other end of the channel could be appropriately discharged or re-circulated after being cooled back to the fluid source for re-use. In this way, the looped portion provides the intended or desired cooling effect.

The catheter devices 100, 200, 500, 600 of the present invention provides advantages over current RF ablation catheters in that the catheter devices of the present invention maintain endocardial contact over a nearly constant radius of distance outside the pulmonary vein ostium. Also, the curvature of any of the catheter devices 100, 200, 500, 600 of the present invention is adjustable so that the catheter device can be adjusted to accommodate the irregularities in the atrial endocardial surface. Further, at all sites the side of the ablation mechanism 130, 230 (e.g., ablation electrode) is held in contact with the endocardial surface, producing larger and more consistent lesions than when the tip of a conventional distal electrode contacts the tissue (as is often the case with current ablation catheters). Furthermore, a family of catheter devices can be manufactured with different radii of curvature. This would enable the user or medical/surgical personnel to choose a catheter device that would provide the appropriate radius of the ring of lesions, depending on the dimensions of the atrium in the individual patient. The design of the catheter devices of the present invention is much simpler than that of inflatable balloon systems, so cost and device failures should be minimized.

Figure 4:
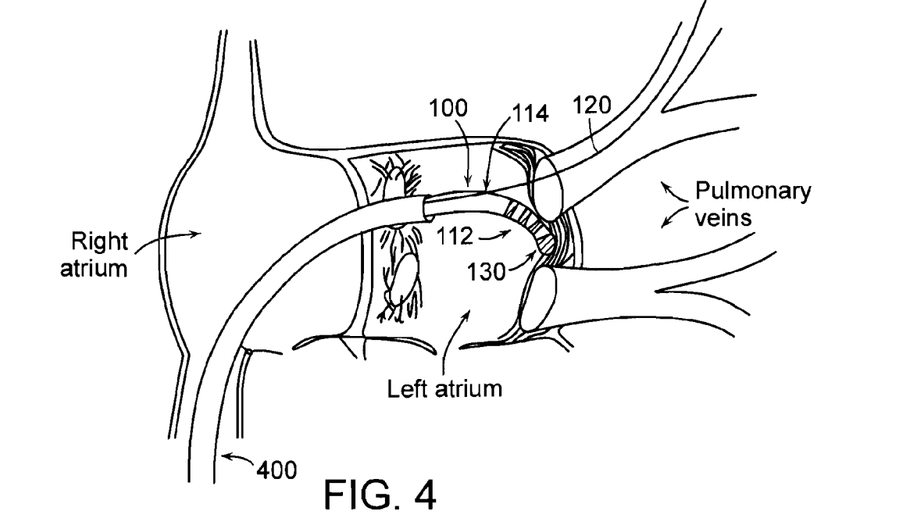
FIG. 4 is an illustrative view of the catheter of the present invention when located within the heart of a mammal.
Figure 7:
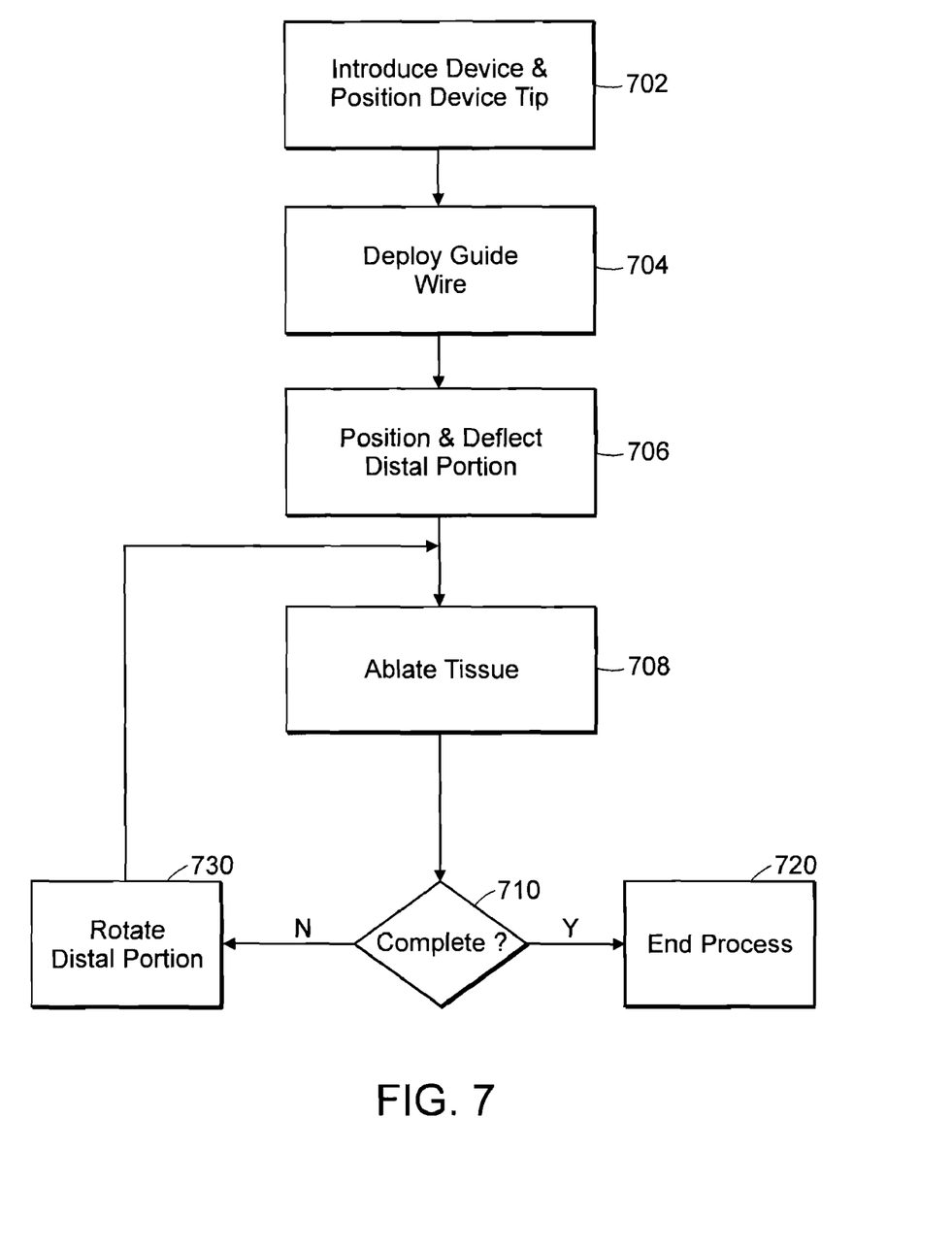
FIG. 7 is illustrative of a treatment methodology according to the present invention.

The use of any of the catheter devices of the present invention as well as the methodology of the present invention can be best understood from the following discussion as well as with reference to FIGS. 4 and 7. Reference also should be made to the foregoing discussion for FIGS. 2, 3 and 5-6 for details of the catheter device not otherwise shown or illustrated in FIGS. 4 and 7.

After preparing the catheter device 100, 200, 500, 600 and other related devices and instrumentalities used in a given surgical or medical procedure, the user/surgeon introduces the catheter device into the body (preferably mammalian body), and manipulates the device so that the tip or distal portion 112, 212 of the elongated body member 110, 210 is appropriately positioned with respect to the target site, Step 702. More specifically, the tip of the distal portion 112, 212 is positioned within the left atrium according to a transeptal access method, which is further described in more detail as follows.

In the transeptal method, the right venous system is first accessed using the "Seldinger" technique, wherein a peripheral vein (such as a femoral vein) is punctured with a needle, the puncture wound is dilated with a dilator to a size sufficient to accommodate an introducer sheath, and an introducer sheath with at least one hemostatic valve is seated within the dilated puncture wound while maintaining relative hemostasis. With the introducer sheath in place, the guiding catheter or transeptal sheath 400 is introduced through the hemostatic valve of the introducer sheath and is advanced along the peripheral vein, into the region of the vena cavae, and into the right atrium.

Once in the right atrium, the distal tip of the guiding catheter or transeptal sheath 400 is positioned against the fossa ovalis in the intraatrial septal wall. A "Brochenbrough" needle or trocar is then advanced distally through the guide catheter until it punctures the fossa ovalis. A separate dilator may also be advanced with the needle through the fossa ovalis to prepare an access port through the septum for seating the guiding catheter/transeptal sheath 400. The guiding catheter/traneptal sheath 400 thereafter replaces the needle across the septum and is seated in the left atrium through the fossa ovalis, thereby providing access for object devices through its own inner lumen and into the left atrium.

It is however further contemplated that other left atrial access methods may be suitable substitutes for using any of the ablation devices 100, 200, 500, 600 of the present invention. In one alternative variation not shown, a "retrograde" approach may be used, wherein the guiding catheter/transeptal sheath 400 is advanced into the left atrium from the arterial system. In this variation, the Seldinger technique is employed to gain vascular access into the arterial system, rather than the venous, for example at a femoral artery. The guiding catheter/transeptal sheath 400 is advanced retrogradedly through the aorta, around the aortic arch, into the ventricle, and then into the left atrium through the mitral valve.

Subsequent to gaining transeptal access to the left atrium as just described, the guide member 120 is deployed, Step 704. More particularly, the elongated body member 110, 210 of the catheter device is advanced through the transeptal sheath 400 into the left atrium, and preferably manipulated into one of the pulmonary veins. Thereafter, the guide member 120 (e.g. a guidewire) is advanced through the particular form of the guiding mechanism (e.g. lumen passage, channel, rail) so that it exits the guiding mechanism (e.g., exits the aperture 114), and is further advanced deep into the vein. In alternative embodiments, the guide member 120 according is advanced into the pulmonary vein by directing it into the vein with a second sub-selective delivery catheter (not shown) which is coaxial within a guiding catheter such as for example by the directional catheters disclosed in U.S. Pat. No. 5,575,766.

Thereafter, the distal portion 112, 212 of the elongated body member 110, 210 is positioned and deflected, Step 706. In more particular embodiments, while the guide member 120 is being maintained in place within the pulmonary vein, the elongated body member 110, 210 is withdrawn from the pulmonary vein until it is back in the left atrial cavity. The distal portion 112, 212 thereof, is then deflected into the desired configuration; such as for example the illustrated curved position. The elongated body member 110 is then advanced axially or longitudinally along the guide member 120, 220 until the side of the deflected portion, including the ablation mechanism 130, is put into contact with the endocardial surface of the atrium, outside the pulmonary vein ostium.

Ablative energy is applied by the ablation mechanism 130 at this site, thereby ablating the targeted tissue, Step 708. After ablating tissue at the given site, the user or surgeon then determines if the surgical procedure is complete, Step 710. If the procedure is not complete (NO, Step 710) then the distal portion 112, 212 of the elongated body member 110, 210 is rotated slightly about the axis of the guide member 120, 220 to a new target site, Step 730 and the process returns to Step 708 so the tissue at the new target site is ablated. This process is repeated until a full ring of lesions has been made.

In alternative embodiments, the catheter device of the present invention is configured and arranged so that the ablative energy from the ablation mechanism 130, 230 can be continuously applied. As such, in this embodiment, the distal portion 112, 212 of the elongated body member is slowly and continuously rotated about the axis defined by the guide member 120. In either embodiment, the guide member 120, 220 serves as an anchor to hold the distal portion 112, 212 of the elongated body member 110, 210 in radially symmetric positions relative to the vein ostium.

If it is determined that the ablating process is completed (YES, Step 710), in other words a full ring of lesions has been formed, the process is ended or stopped, Step 720. If the particulars of the surgical procedure involve the targeting of more than one area or pulmonary vein, then the distal portion 112, 212 is repositioned and the above process is repeated for each of the pulmonary veins being targeted.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A catheter device comprising:
an elongated body member having a distal portion and an end;
a guide member;
a guiding mechanism coupled to the elongated body member and configured so as to guide the guide member;
wherein the guiding mechanism includes an exit portion from which the guide member exits when the guide member is being deployed from the guiding mechanism, where the exit portion is disposed with respect to the distal portion so the distal portion deflects from and with respect to the guide member, when the guide member is in deployed condition;
wherein the distal portion is that portion of the elongated body member extending from the guiding mechanism exit portion to the end of the elongated body member; and
a deflection mechanism that extends within the elongated body and is operably coupled to the distal portion so as to cause the distal portion to deflect with respect to a longitudinal axis of the elongated body member.

2. The catheter device of claim 1, wherein the guiding mechanism comprises a channel within the elongated body member and the exit portion comprises a through aperture in a side of the elongated body member that is in communication with the channel, where the guide member is deployed from the through aperture.

3. The catheter device of claim 1, wherein the guiding mechanism comprises an artifact on the external surface of the elongated body member and extending axially along the elongated body member, where the artifact and the guide member are configured and arranged so the guide member is moveably retained by the artifact and so as to allow for deployment of the guide member.

4. A catheter device comprising:
an elongated body member having a distal portion and an end;
a guide member;
a guiding mechanism coupled to the elongated body member and configured so as to guide the guide member;
an ablation device being disposed in the distal portion, the ablation device being configured and arranged to ablate tissues proximal the ablation device;
wherein the guiding mechanism includes an exit portion from which the guide member exits when the guide member is being deployed from the guiding mechanism;
wherein the distal portion is that portion of the elongated body member extending from the guiding mechanism exit portion to the end of the elongated body member;
a deflection mechanism that extends within the elongated body and is operably coupled to the distal portion so as to cause the distal portion to deflect with respect to a longitudinal axis of the elongated body member;
wherein the exit portion is disposed with respect to the distal portion so the distal portion deflects from and with respect to the guide member, when the guide member is in deployed condition; and
wherein the exit portion is configured and arranged so that the distal portion when in a deflected condition is rotatable about the guide member, when the guide member is in a deployed condition.

5. The catheter device of claim 4, wherein the guiding mechanism comprises a channel within the elongated body member and the exit portion comprises a through aperture in a side of the elongated body member that is in communication with the channel, where the guide member is deployed from the through aperture.

6. A method for ablating tissue in particular atrial tissue, comprising the steps of:
providing a deflection catheter device that includes a deflectable distal portion, a deflection mechanism that extends within the deflection catheter device and operably coupled to the deflectable distal portion, an ablation device disposed within the deflectable distal portion and a guide member, wherein the deflectable distal portion includes an end thereof;
deploying the guide member so at least a distal portion thereof is deployed through an opening in, and disposed in, a chamber, vessel or vein of a body; and
deflecting the deflectable distal portion including the end thereof with respect to the guide member using the deflection mechanism.

7. The tissue ablating method of claim 6, wherein the provided deflection catheter device further includes a body member and a guiding mechanism, wherein the guiding mechanism includes a channel within the body member and a through aperture in a side of the body member that is in communication with the channel, wherein said deploying includes deploying the guide member from the through aperture.

8. The tissue ablating method of claim 6, further comprising the step(s) of:
contacting a tissue area including tissues to be ablated with at least a part of the deflected deflectable distal portion, where the ablation device is disposed within the part; and
actuating the ablation device.

9. The tissue ablating method of claim 8, further comprising the step(s) of:
rotating the deflected deflectable distal portion about the guide member; and
wherein said contacting includes contacting another tissue area.

10. The tissue ablating method of claim 9, further comprising the steps(s) of:
de-activating the ablation device during said rotating; and
activating the ablation device after contacting said another tissue area.

11. The tissue ablating method of claim 8, further comprising the step(s) of:
rotating the deflected deflectable distal portion about the guide member; and
maintaining the ablation device in an activated condition as the deflected deflectable distal portion is being rotated about the guide member.

12. The tissue ablating method of claim 11, further comprising the step(s) of:
re-configuring the deflectable distal portion during said rotating so as to maintain the at least a part of the distal portion in contact with the tissues.

13. A method for ablating tissue in particular atrial tissue, comprising the steps of:
providing a deflection catheter device that includes a deflectable distal portion, an ablation device disposed within the deflectable distal portion, a guide member and a guiding mechanism that moveably retains at least a portion of the guide member;
wherein the deflectable distal portion extends from an exit portion of the guiding mechanism to an end of the deflectable distal portion;
localizing an end of the deflectable distal portion with respect to an opening in a chamber, vessel or vein of a mammalian body;
deploying the guide member from the guiding mechanism so at least a distal portion thereof is deployed through the opening in, and is disposed in, the chamber, vessel or vein of the mammalian body;
deflecting the deflectable distal portion with respect to the guide member;
contacting a tissue area including tissues to be ablated with at least a part of the deflected deflectable distal portion, where the ablation device is disposed within said at least a part;
and actuating the ablation device.

14. The tissue ablating method of claim 13, wherein the provided deflection catheter device further includes a body member, wherein the guiding mechanism includes a channel within the body member and a through aperture in a side of the body member that is in communication with the channel, and wherein said deploying includes deploying the guide member from the through aperture.

15. The method of claim 13, further comprising the steps of:
monitoring electrical conduction signals along a pulmonary vein; and identifying an origin of atrial arrhythmias as being located in the pulmonary vein based upon the monitored conduction signals.

16. The tissue ablating method of claim 13, further comprising the step(s) of:
rotating the deflectable distal portion about the guide member; and
wherein said contacting includes contacting another tissue area.

17. The tissue ablating method of claim 16, further comprising the step(s) of:
de-activating the ablation device during said rotating; and
activating the ablation device after contacting said another tissue area.

18. The tissue ablating method of claim 13, further comprising the step(s) of:
rotating the deflected deflectable distal portion about the guide member; and
maintaining the ablation device in an activated condition as the deflected deflectable distal portion is being rotated about the guide member.

19. The tissue ablating method of claim 18, further comprising the step(s) of:
re-configuring the deflectable distal portion during said rotating so as to maintain the at least a part of the deflectable distal portion in contact with the tissues.

20. A method for treating arrhythmias, comprising the step(s) of:
providing a deflection catheter device that includes a deflectable distal portion having an end thereof, an ablation device disposed within the deflectable distal portion and a guide member;
deploying the guide member so at least a distal portion thereof is deployed through an opening in, and disposed in, a vein of a mammalian body;
deflecting the deflectable distal portion including the end thereof with respect to the guide member.

21. The method of claim 20, wherein the provided deflection catheter device further includes a body member and a guiding mechanism, wherein the guiding mechanism includes a channel within the body member and a through aperture in a side of the body member that is in communication with the channel, and wherein said deploying includes deploying the guide member from the through aperture.

22. The method of claim 20, further comprising the step(s) of:
contacting a tissue area including tissues to be ablated with at least a part of the deflectable distal portion, where the ablation device is disposed within the part; and
actuating the ablation device.

23. The method of claim 22, further comprising the step(s) of:
rotating the deflectable distal portion about the guide member; and
wherein said contacting includes contacting another tissue area.

24. The method of claim 23, further comprising the step(s) of:
de-activating the ablation device during said rotating; and
activating the ablation device after contacting said another tissue area.

25. A method for treating arrhythmias, comprising the step(s) of:
providing a deflection catheter device that includes a deflectable distal portion having an end, an ablation device disposed within the deflectable distal portion, a guide member and a guiding mechanism that moveably retains at least a portion of the guide member;
localizing the end of the deflectable distal portion within the left atrium of a mammalian body and with respect to an opening in a vein;
deploying the guide member from the guiding mechanism so at least a distal portion thereof is deployed through the opening in, and is disposed in, the vein;
wherein the deflectable distal portion extends from an exit portion of the guiding mechanism to the end of the deflectable distal portion;
deflecting the deflectable distal portion including the end with respect to the guide member;
contacting a tissue area including tissues to be ablated with at least a part of the deflectable portion, where the ablation device is disposed within the part; and
actuating the ablation device.

26. The method of claim 25, wherein the provided deflection catheter device further includes a body member, wherein the guiding mechanism includes a channel within the body member and a through aperture in a side of the body member that is in communication with the channel, and wherein said deploying includes deploying the guide member from the through aperture.

27. The method of claim 25, further comprising the step(s) of:
rotating the deflected deflectable distal portion about the guide member; and
wherein said contacting includes contacting another tissue area.

28. The method of claim 27, further comprising the step(s) of:
de-activating the ablation device during said rotating; and
activating the ablation device after contacting said another tissue area.

29. The method of claim 27, further comprising the step of maintaining the ablation device in an activated condition as the deflected deflectable distal portion is being rotated about the guide member.

30. A method for treating left atrial arrhythmia in a left atrium of a mammalian body; comprising the steps of:
providing a deflection catheter device that includes a deflectable distal portion having an end, an ablation device disposed within the deflectable distal portion, a guide member and a guiding mechanism that moveably retains at least a portion of the guide member;
introducing a portion of the catheter device including the deflectable distal portion into the left atrium;
positioning an end of the deflectable distal portion with respect to an a pulmonary vein extending from the left atrium;
deploying the guide member from the guiding mechanism so at least a distal portion thereof is deployed through the opening in, and is disposed in, the pulmonary vein;
deflecting the deflectable distal portion with respect to the guide member;
wherein the deflectable distal portion extends from an exit portion of the guiding mechanism to the end of the deflectable distal portion;
contacting a tissue area including tissues to be ablated with at least a part of the deflectable portion, where the ablation device is disposed within the part; and
actuating the ablation device.

31. The method of claim 30, further comprising the step(s) of:
rotating the deflected deflectable distal portion about the guide member; and wherein said contacting includes contacting another tissue area.

32. The method of claim 31, further comprising the step(s) of:
de-activating the ablation device during said rotating; and
activating the ablation device after contacting said another tissue area.

33. The method of claim 31, further comprising the step of maintaining the ablation device in an activated condition as the deflected deflectable distal portion is being rotated about the guide member.

34. The method of claim 30, wherein the provided deflection catheter device further includes a body member, wherein the guiding mechanism includes a channel within the body member and a through aperture in a side of the body member that is in communication with the channel, and wherein said deploying includes deploying the guide member from the through aperture.

* * * * *